United States Patent
Matsubayashi et al.

(10) Patent No.: US 10,532,079 B2
(45) Date of Patent: Jan. 14, 2020

(54) EXTRACTS AND BEVERAGES CONTAINING 2,5-PIPERAZINEDIONE, 3,6-BIS(PHENYLMETHYL)-, (3S,6S)-

(71) Applicants: SUNTORY HOLDINGS LIMITED, Osaka (JP); CEREBOS PACIFIC LIMITED, China Square Central (SG)

(72) Inventors: Hideki Matsubayashi, China Square Central (SG); Kenji Yamamoto, Kanagawa (JP); Hiroshi Watanabe, Tokyo (JP); Lee Kian Hong, China Square Central (SG)

(73) Assignees: SUNTORY HOLDINGS LIMITED, Osaka (JP); SUNTORY BEVERAGE & FOOD ASIA PTE. LTD., Singapore (SG)

( * ) Notice: Subject to any disclaimer, the term of this patent is extended or adjusted under 35 U.S.C. 154(b) by 0 days.

(21) Appl. No.: 15/082,526

(22) Filed: Mar. 28, 2016

(65) Prior Publication Data

US 2016/0206685 A1 Jul. 21, 2016

Related U.S. Application Data

(63) Continuation of application No. 13/516,488, filed as application No. PCT/JP2010/053592 on Feb. 26, 2010, now abandoned.

(30) Foreign Application Priority Data

Dec. 25, 2009 (JP) ................. 2009-296287

(51) Int. Cl.
A61K 38/12 (2006.01)
A23L 2/66 (2006.01)
A61K 9/00 (2006.01)

(52) U.S. Cl.
CPC ............... *A61K 38/12* (2013.01); *A23L 2/66* (2013.01); *A61K 9/0095* (2013.01); *A23V 2002/00* (2013.01)

(58) Field of Classification Search
CPC .................... A61K 38/12; A23L 2/66
See application file for complete search history.

(56) References Cited

U.S. PATENT DOCUMENTS

| 4,006,261 | A | 2/1977 | Pickenhagen et al. |
| 2005/0255225 | A1* | 11/2005 | Fujimoto ............... A23L 13/30 426/655 |
| 2012/0282387 | A1 | 11/2012 | Matsubayashi et al. |
| 2012/0283178 | A1 | 11/2012 | Tsuruoka et al. |

FOREIGN PATENT DOCUMENTS

| GB | 1 420 909 | 1/1976 | |
| JP | 50058271 | 5/1975 | |
| WO | 2011077760 | 6/2011 | |
| WO | WO-2011077759 A1 * | 6/2011 | ............... A23L 2/52 |

OTHER PUBLICATIONS

International Search Report for PCT/JP2010/053592, dated Apr. 27, 2010.
Japanese Patent Application No. 2009-296164, filed Dec. 25, 2009.
SciFinder; CAS Registry No. 2862-51-3; 2,5-Piperazinedione, 3,6-bis(phenylmethyl)-, (3S,6S)-registry record; accessed Jan. 12, 2016.
Rødbotten et al.; "A cross-cultural study of preference for apple juice with different sugar and acid contents"; 2008; Food Quality and Preference; 20:277-284.
http://www.topac.com/salinity_brix.html, accessed Jan. 12, 2016.
Euguchi et al.; "Studies on Cyclic Dipeptides. I. Thermodynamics of the Cis-Trans Isomerization of the Side Chains in Cyclic Dipeptides"; 1974; Journal of the American Chemical Society; 96(12): 3985-3989.
Yanes et al.; "Effect of hydroclloid type and concentration on flow behavior and sensory properties of milk beverages model systems"; 2002; Food Hydrocolloids; 16; 605-611.
"Extract": Oxford Dictionary; http://oxforddictionaries.com/us/definition/american_english/extract; accessed Aug. 21, 2013.
Chen et al.; "Two-step mass spectrometric approach for the identification of diketopiperazines in chicken essence"; 2004; Eur. Food Res. Technol.; 218: 589-597.

* cited by examiner

*Primary Examiner* — Timothy P Thomas
(74) *Attorney, Agent, or Firm* — Greenblum & Bernstein, P.L.C.

(57) ABSTRACT

Extracts or beverages whose ratio between the content of 2,5-piperazinedione,3,6-bis(phenylmethyl)-,(3S,6S)-(unit: μg/100 g) and Brix (Bx) is 6 (μg/100 g)/Bx or more are good in flavor and feeling on the tongue and further have a good appearance.

10 Claims, 2 Drawing Sheets

EXTRACTS AND BEVERAGES CONTAINING 2,5-PIPERAZINEDIONE, 3,6-BIS(PHENYLMETHYL)-, (3S,6S)-

This application is a continuation of U.S. application Ser. No. 13/516,488 filed on Jun. 5, 2012, which was a 371 of International Application No. PCT/JP2010/053592 filed on Feb. 26, 2010, which claims the benefit of Japanese Patent Application No. 2009-296287 filed on Dec. 25, 2009. The disclosures of these documents, including the specifications, drawings, and claims, are expressly incorporated herein by reference in their entireties.

TECHNICAL FIELD

The present invention relates to foods and beverages containing 2,5-piperazinedione,3,6-bis(phenylmethyl)-,(3S, 6S)-, and more particularly relates to extracts and beverages containing 2,5-piperazinedione,3,6-bis(phenylmethyl)-,(3S, 6S)- at a high concentration, wherein the pH is 5 or more.

BACKGROUND ART

In a highly complex modern society, a reduction of willingness turns into a problem. For example, the term "motivation crisis" is used to describe the problem of reduced motivation in young people. Moreover, it is said that depression patients often show symptoms of hypobulia, and there is a demand for the development of drugs capable of improving hypobulia.

In recent years, a "dipeptide" composed of two amino acids attached to each other has received attention as a functional substance. Dipeptides can be designed to have additional physical properties and/or new functions, which cannot be seen in single amino acids, and hence they are expected to be applicable to a wider range than that of amino acids. The inventors of the present invention have found that a 2,5-diketopiperazine derivative, i.e., 2,5-piperazinedione, 3,6-bis(phenylmethyl)-,(3S,6S)-(CA Registry Number: 2862-51-3) (hereinafter referred to as "compound A") has an improving effect on learning motivation (the co-filed patent application: Japanese Patent Application No. 2009-296164).

Products known to contain compound A include chicken extracts in liquid form which are obtained by decocting meat of livestock, as well as chicken consomme and the like in solid form.

SUMMARY OF INVENTION

Technical Problem

However, in order that compound A contained in these chicken extracts or chicken consomme is incorporated at a high concentration into foods and beverages, it is necessary to add chicken extracts or consomme cubes in large amounts. When added in such large amounts, the taste or slack peculiar to chicken extracts or consomme cubes will considerably affect the flavor of foods and beverages, and the latitude in flavor design for foods and beverages is substantially lost.

In addition, if the decoction time is simply extended by the conventional method in order to increase the content of compound A in chicken extract, not only the concentration of compound A but also those of other substances (e.g., bitter components) will increase. Liquids that contain various substances mixed at high concentrations, i.e., liquids that have high Bx values are in themselves unsuitable as beverages; even when added to beverages, they affect the flavor or feeling on the tongue of the beverages so greatly that they are unsuitable for use in beverages.

Moreover, compound A is hardly soluble in water and hence cannot be simply added as such when attempting to incorporate compound A, which is a useful substance with an improving effect on learning motivation, into beverages at a high concentration and in an easy-to-ingest form.

In view of the foregoing, the present invention aims to provide an extract or beverage containing compound A, which is a useful substance with an improving effect on learning motivation, in an easy-to-ingest form and at a high concentration.

Solution to Problem

As a result of extensive and intensive efforts made to solve the problems stated above, the inventors of the present invention have succeeded in obtaining extracts and beverages, which not only contain compound A at a high concentration but also have low Bx values and which are good in flavor and feeling on the tongue and further have a good appearance. This success led to the completion of the present invention.

Namely, the present invention is directed to [1] to [15] shown below.

[1] An extract containing compound A and having a pH of 5 or more, wherein the ratio between the content of compound A (unit: μg/100 g) and Brix (Bx) is 6 (μg/100 g)/Bx or more.

[2] The extract according to [1] above, which contains compound A at a concentration of 60 μg/100 g or more.

[3] The extract according to [1] or [2] above, wherein compound A is extracted from a naturally occurring product.

[4] The extract according to [3] above, wherein the naturally occurring product is meat of livestock or poultry, fish meat, or shellfish meat.

[5] The extract according to [3] or [4] above, wherein the naturally occurring product is chicken meat.

[6] A dried extract obtainable by drying the extract according to any one of [1] to [5] above.

[7] A capsule or tablet encapsulating the extract according to any one of [1] to [5] above or the dried extract according to [6] above. [8] A beverage obtainable by addition of the extract according to any one of [1] to [5] above.

[9] A beverage containing compound A and having a pH of 5 to 10, wherein the ratio between the content of compound A (unit: μg/100 g) and Brix (Bx) is 6 (μg/100 g)/Bx or more.

[10] The beverage according to [8] or [9] above, which contains compound A in an amount of 60 μg/100 g or more.

[11] A packaged beverage, wherein the beverage according to any one of [8] to [10] above is packed in a container.

[12] A process for producing the extract according to [1] above, which comprises:

(1) a pretreatment step in which meat of livestock or poultry, fish meat or shellfish meat is used as a starting material and heated in a liquid to remove water-soluble proteins contained therein, (2) a heating step in which the liquid is replaced after the pretreatment and heating is repeated again, and (3) a filtration step in which the obtained liquid sample is filtered. [13] A process for producing the extract according to [1] above, which comprises:

(1) a pretreatment step in which meat of livestock or poultry, fish meat or shellfish meat is used as a starting material and heated in a liquid to remove water-soluble proteins contained therein, (2) a heating step in which the liquid is replaced after the pretreatment and heating is repeated again, (3) a filtration step in which the obtained liquid sample is filtered, and (4) a concentration step.

[14] A process for producing the beverage according to [9] above, which comprises:

(1) a pretreatment step in which meat of livestock or poultry, fish meat or shellfish meat is used as a starting material and heated in a liquid to remove water-soluble proteins contained therein, (2) a heating step in which the liquid is replaced after the pretreatment and heating is repeated again, and (3) a filtration step in which the obtained liquid sample is filtered.

[15] A process for producing the beverage according to [9] above, which comprises:

(1) a pretreatment step in which meat of livestock or poultry, fish meat or shellfish meat is used as a starting material and heated in a liquid to remove water-soluble proteins contained therein, (2) a heating step in which the liquid is replaced after the pretreatment and heating is repeated again, (3) a filtration step in which the obtained liquid sample is filtered, and (4) a concentration step.

Advantageous Effects of Invention

The present invention provides extracts and beverages, in which compound A having an improving effect on learning motivation and being highly safe without side effects can be contained at a high content with Bx values remaining low. The extracts of the present invention can be added to beverages and so on without impairing the taste inherent to foods and beverages. The extracts or beverages of the present invention, as well as foods and beverages comprising the same can be ingested continuously over a long period of time as foods and beverages useful for improvement of learning motivation.

DESCRIPTION OF EMBODIMENTS

A detailed explanation will be given below for the embodiments of the present invention.

<Extract>

The extract of the present invention contains compound A, which is a useful substance with an improving effect on learning motivation, at a high content and in an easy-to-ingest form. More specifically, it is an extract which contains compound A at a high concentration and whose ratio between the content of compound A (unit: µg/100 g) and Brix (Bx) is 6 (µg/100 g)/Bx or more.

Since compound A is a useful substance with an improving effect on learning motivation, it is more desirable to have a higher content in the extract. More specifically, the content is preferably 60 µg/100 g or more, and more preferably 75 µs/100 g or more. However, an extract with a high Brix value means that various substances (e.g., bitter components) originating from starting materials are contained at high concentrations, and such an extract is in itself unsuitable as a beverage and also affects the flavor or feeling on the tongue so greatly that it is unsuitable for use in beverages. Thus, a lower Brix value is more desirable. It should be noted that "Bx" used herein can be determined with a commercially available Bx meter.

Thus, preferred is an extract being rich in compound A, which is a useful substance, and having a low Brix value, i.e., an extract whose ratio between the content of compound A (unit: µg/100 g) and Brix (Bx) is high. More specifically, the ratio between the content of compound A (unit: µg/100 g) and Brix (Bx) is preferably 6 (µg/100 g)/Bx or more, and more preferably 10 (µg/100 g)/Bx or more.

The concentration of compound A can be quantified in various manners, for example, by high performance liquid chromatography (HPLC).

The extract of the present invention is advantageous in that it can be incorporated in small amounts into beverages and allows more latitude in beverage design because of its relatively low Bx value although it contains compound A at a high content. As a result, it is possible to prepare beverages which are excellent in appearance (causing no sediment or turbidity) and whose flavor is not impaired.

Moreover, the extract of the present invention preferably has a pH of 5 or more such that it leaves no sediment, e.g., when added to a liquid of neutral pH. Likewise, the pH is preferably 10 or less, and more preferably 8 or less for direct ingestion.

The term "extract" used herein is intended to mean a liquid extract, which may be ingested as such or may be added to foods and beverages. In addition, the extract can be easily converted into a powder form through a step of lyophilization or freeze-drying, etc. The resulting extract powder is water-soluble and can be easily dissolved in a liquid of pH 5 or more (e.g., water) before ingestion. Moreover, conversion into a powder form facilitates addition of the extract to various foods and beverages, and allows easy use of the extract.

Alternatively, the form of soft capsules or tablets is also possible. Soft capsules or tablets encapsulate the extract of the present invention, or an extract powder or granule thereof.

There is no limitation on the type or form of foods and beverages into which the extract or extract powder is incorporated. For example, they can be provided in the form of health foods in a tablet form (e.g., tablets and capsules), solid foods including yogurt, processed foods, desserts and sweets (e.g., gum, candy, jelly), liquid beverages including coffee, oolong tea, tea, soft drinks and drinkable preparations. Moreover, pet foods and animal feeds are also included.

<Beverage>

The present invention is directed to a beverage which contains compound A and whose ratio of compound A content/Bx is 6 (µg/100 g)/Bx or more, and more particularly a beverage which contains compound A in an amount of 60 µg/100 g or more.

The beverage of the present invention is good in flavor and feeling on the tongue and further has a good appearance. The beverage of the present invention also has an improving effect on learning motivation and can be ingested continuously over a long period of time.

The pH of the beverage of the present invention is not limited in any way, but it preferably ranges from 5 to 10.

The beverage of the present invention can be provided in the form of a packaged beverage, as in the case of conventional beverages.

<Production Process for Extract or Beverage>

The present invention is directed to an extract or beverage containing compound A, in which the concentration of compound A can be increased even at a low Bx value. Such an extract or beverage can be prepared, for example, by the production process shown below:

(1) a pretreatment step in which meat of livestock or poultry, fish meat or shellfish meat is used as a starting material and heated in a liquid to remove water-soluble proteins contained therein, (2) a heating step in which the liquid is replaced after the pretreatment and heating is repeated again, and (3) a filtration step in which the obtained liquid sample is filtered, (4) a concentration step, if necessary.

A preferred starting material used in the above pretreatment step (1) is a naturally occurring product from which compound A, a useful component, can be efficiently obtained, particularly meat of livestock or poultry, fish meat, or shellfish meat. Examples of meat of livestock or poultry include meat of livestock, i.e., cattle, pig, horse, sheep or goat, meat of non-livestock animals such as wild boar or deer, meat of poultry, i.e., chicken, turkey, quail, domestic duck or crossbred duck, as well as meat of non-poultry wild birds such as wild duck, pheasant, sparrow or thrush. Likewise, it is also possible to use fish meat and shellfish meat which are eaten in the course of a normal diet. As other examples, plant materials such as coffee and cocoa can also be used. Among these examples for meat of livestock or poultry, fish meat and shellfish meat, chicken meat is preferred for use because compound A can be efficiently obtained at a high concentration.

Although the reason why compound A is obtained in large amounts when using chicken meat is unknown, it is inferred that proteins in chicken meat are rich in the contiguous phenylalanine (-Phe-Phe-) structure and thereby generate a dipeptide (Phe-Phe) in abundance, as a result of which compound A of interest will be obtained in large amounts.

In the pretreatment step (1), any treatment for reducing water-soluble proteins contained in a starting material may be performed, for example, by boiling in water at 100° C. to 160° C. for 30 minutes to several hours (preferably about 3 to 8 hours, more preferably about 3 to 4 hours). As a heating device, a pressure cooker, an autoclave and so on can be combined for use depending on the intended conditions. Moreover, there is no limitation on the number of liquid replacements performed in the pretreatment step (1). For example, during the step (1), an additional liquid (e.g., water) or an additional starting material may further be added to adjust the concentration of an extract or beverage.

The heating step (2) is preferably accomplished at a high temperature under a high pressure (100° C. or more and 1 atm or more), for example, at 100° C. or more, and more preferably at 125° C. or more. In addition, the heating time in the heating step (2) preferably ranges from 30 minutes to several hours, more preferably from about 3 to 7 hours. As a heating device, a pressure cooker, an autoclave and so on can also be combined for use depending on the intended conditions.

The pretreatment step (1) and the heating step (2) may be performed continuously as a single step without liquid replacement. Alternatively, the pretreatment step may be followed by removal of the pre-treated meat and then replacement of the liquid before the meat is subjected to the heating step. Since samples with lower Brix values can be obtained when liquid replacement is performed after the pretreatment step (1) and before the heating step (2), it is more desirable to use liquid replacement. Moreover, in the case of using the concentration step so as to enrich compound A, it is also more desirable to use liquid replacement between the pretreatment step (1) and the heating step (2) because good results will be obtained in terms of overall flavor including bitterness and slack, and the resulting samples will be less likely to affect the flavor of beverages upon addition.

It should be noted that heat treatment in the steps (1) and (2) is preferably performed in a solvent in order to prevent plant and animal materials from burning. Examples of a solvent preferred for use include water, ethanol, or mixtures thereof. Namely, a plant or animal material containing proteins (preferably proteins rich in the contiguous phenylalanine (-Phe-Phe-) structure) is mixed with a solvent and subjected to heat treatment, followed by collection of the solvent to obtain a solution rich in compound A.

The power of filtration in the filtration step (3) may be selected as appropriate, depending on the form of foods into which the resulting extract is incorporated, and the filtration method may also be determined as appropriate by those skilled in the art. For example, in cases where the extract is used for solid foods (e.g., tablets) and where the resulting beverages do not need to be clear (e.g., canned beverages whose appearance is hidden in containers), it is sufficient to filter off sediments and filtration through a strainer may be used for this purpose. Alternatively, in a case where the extract needs to be clear (e.g., used for beverages in transparent bottles or plastic bottles), powerful filtration should be used. For clarification purposes, filtration through a strainer may be followed by filtration through a membrane (ion exchange membrane, RO membrane, zeta potential membrane) and/or filtration through diatomaceous earth, etc.

In the extract or beverage of the present invention, this solution rich in compound A may be used directly or, if necessary, may be concentrated to further increase the concentration of compound A. The concentration step (4) may be accomplished by using an evaporator or by lyophilization, etc. After the concentration step (4), the resulting concentrate may be added to another liquid to produce the beverage of the present invention.

It should be noted that the content of compound A increases before and after concentration, whereas the ratio between the content of compound A (unit: μg/100 g) and Brix (Bx) remains substantially unchanged. This is because the Brix (Bx) value also increases upon concentration. Thus, when samples whose ratio between the content of compound A (unit: μg/100 g) and Brix (Bx) is 6 (μg/100 g)/Bx or more are concentrated, it is possible to obtain extracts containing a higher content of compound A and having a ratio of 6 (μg/100 g)/Bx or more. In contrast, when samples whose ratio between the content of compound A (unit: μg/100 g) and Brix (Bx) is less than 6 (μg/100 g)/Bx are concentrated, it is not possible to obtain extracts whose ratio between the content of compound A (unit: μg/100 g) and Brix (Bx) is 6

(μg/100 g)/Bx or more, although extracts containing a high content of compound A are obtained.

Moreover, the extract and beverage of the present invention are intended to contain compound A in a dissolved state and have a Bx value of 0.01 or more.

The beverage of the present invention may be provided as appropriate in the form of a packaged beverage, when needed.

The present invention will be further described in more detail by way of the following examples, which are not intended to limit the present invention.

EXAMPLES

Example 1

Improving Effect of Compound A on Learning Motivation (1)

Compound A was evaluated for its enhancing effect on learning motivation by the method known in the art, i.e., Morris Water Maze (MWM).

First, water which had been colored black with Indian ink was filled into a cylindrical tank of 90 cm diameter and 35 cm height to give a water depth of 20 cm, and the water temperature was set to 22±1° C. To this tank, C57BL/6 mice (male, 9 weeks of age) were each transferred and allowed to experience open space swimming (OSS). Upon OSS, mice will cause changes in their behavior and enter a state corresponding to depression. After repeating OSS for 5 days, the mice were divided into 7 groups.

Next, in the above cylindrical tank of 90 cm diameter and 35 cm height, an escape platform of 10 cm diameter was placed at a water depth of 0.5 cm. The above 7 groups of mice were each orally administered with compound A (Bachem AG (Bubendorf, Switzerland)) or with a comparative drug, fluvoxamine maleate. After 60 minutes, each mouse was transferred to the tank provided with the escape platform, and measured for the time required to find out the invisible escape platform placed below the water surface (i.e., the time required to reach the escape platform) to evaluate the spatial memory and learning ability of each mouse (MWM). As control mice, animals experiencing no OSS were administered with physiological saline and subjected to MWM. MWM was repeated five times a day for 10 days.

Figure 1:
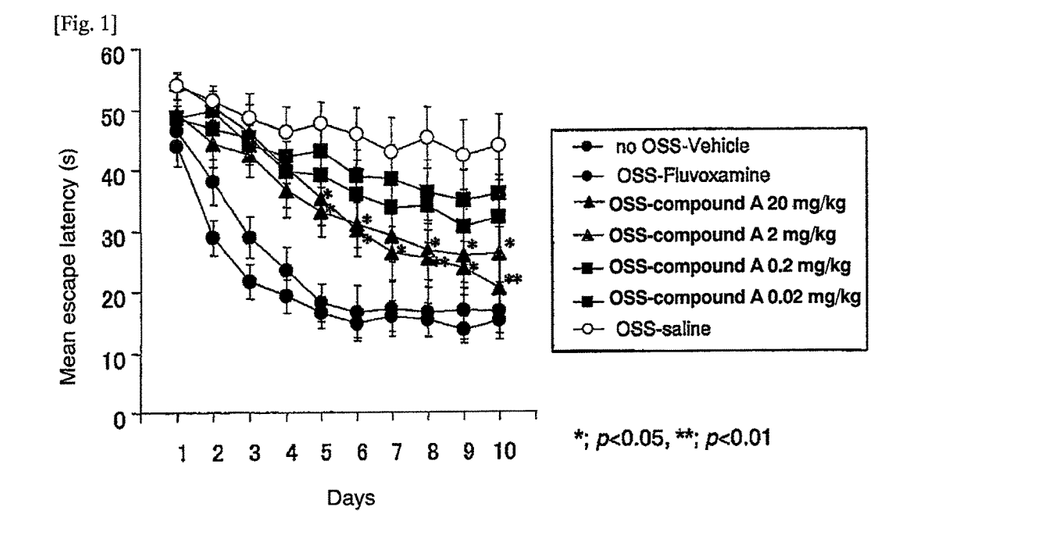
FIG. 1 shows the test results of whether the ingestion of a test sample reduces the time required for mice to find out an escape platform when repeating the test.

The results obtained are shown in FIG. 1. As can be seen from FIG. 1, in the mice experiencing no OSS (no OSS-Vehicle), the time required to find out the escape platform was reduced when repeating the test, whereas the mice experiencing OSS showed reduced learning motivation and there was no reduction in the time required to reach the escape platform (OSS-Saline). In contrast, the group receiving compound A showed a dose-dependent reduction in the time required to reach the escape platform. In the 0.02 mg/kg group, the time required to reach the escape platform at 10 days of MWM was reduced by around 20%, when compared to the control group (OSS-Saline) in which animals experiencing OSS were administered with physiological saline. Moreover, in the 20 mg/kg group, the time required to reach the escape platform at 10 days of MWM was substantially the same as that of the group (OSS-Fluvoxamine) receiving fluvoxamine maleate, which is frequently used as SSRI. This indicates that compound A has an enhancing effect on learning motivation.

Example 2

Improving Effect on Learning Motivation (2)

In the same manner as shown in Example 1, mice were administered with 20 mg/kg compound A and then subjected to the MWM test. As a control, a linear dipeptide (Phe-Phe) was administered at 20 mg/kg, followed by the MWM test.

Figure 2:
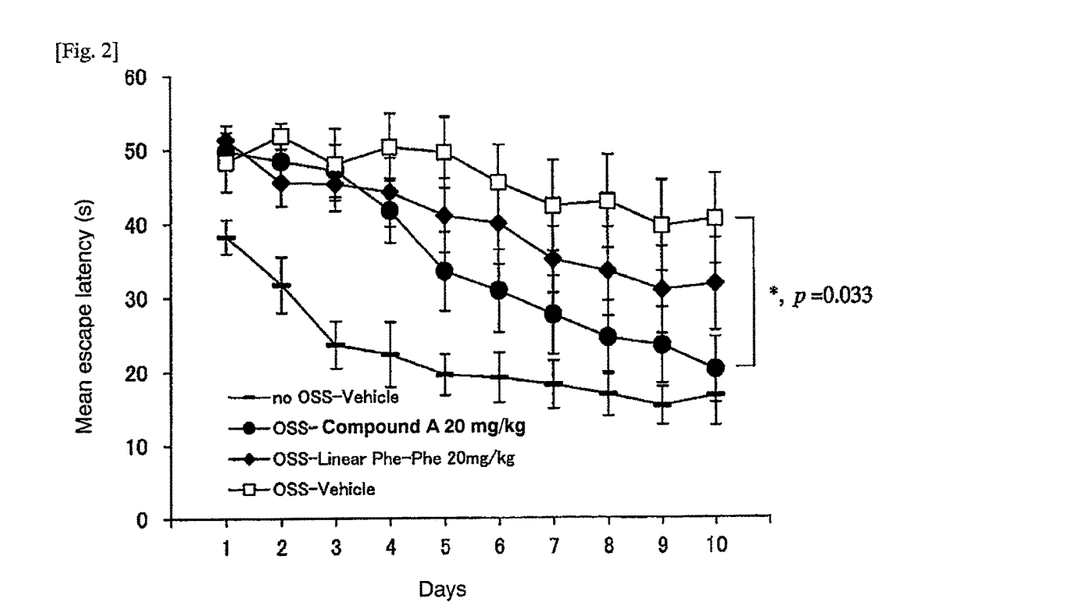
FIG. 2 shows the test results of whether the ingestion of a test sample reduces the time required for mice to find out an escape platform when repeating the test.

The results obtained are shown in FIG. 2. As can be seen from FIG. 2, the linear dipeptide (Phe-Phe) was not confirmed to have a significant effect, whereas compound A showed a significant improving effect on learning motivation over the control group (OSS-Saline). Namely, it is indicated that the cyclic dipeptide structure is required for exerting an improving effect on learning motivation.

Example 3

Study on Starting Materials

Figure 3:
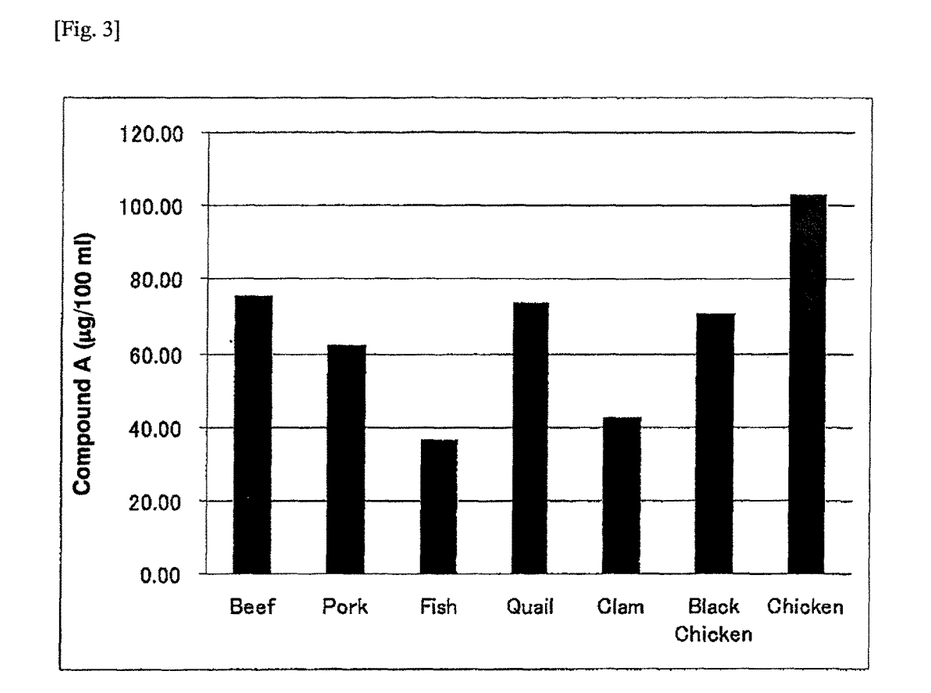
FIG. 3 shows the quantification results of compound A in extracts obtained with various starting materials.

As protein-containing starting materials, beef meat, pork meat, fish, quail meat, corbicula clam and chicken meat (Black Chicken, Chicken) were used. Each animal material was mixed with one volume of water and introduced into a container, followed by heat treatment in an autoclave at 135° C. for 4 hours (as a pretreatment step) and further at 135° C. for 4 hours (as a heating step). The heat-treated liquid was collected and eluted with acetonitrile from a pretreatment column (OASIS MAX (Waters: 30 mg/1 cc)), followed by high performance liquid chromatography (HPLC) to quantify the content of compound A. Conditions for HPLC are as shown below. The results obtained are shown in FIG. 3.

(HPLC Conditions)
System: Agilent 1100 series
Column: Develosil C30-UG-5 (4.6×150 mm, 5 μm)
Mobile phase A: water, Mobile phase B: 100% acetonitrile solution
Gradient:

| Time (min) | Solvent B |
| --- | --- |
| 0.00 | 20% |
| 9.00 | 20% |
| 23.00 | 28% |
| 24.00 | 70% |
| 31.00 | 70% |
| 31.10 | 20% |
| 40.00 | 20% |

Injection volume: 10 μl
UV detector wavelength: 215 nm
Flow rate: 1.0 ml/min
Column temperature: 32° C.

It should be noted that a compound A-containing liquid can also be collected from roasted coffee beans themselves, whereas compound A was not detected in coffee beverages extracted from roasted beans.

Example 4

Production of Extracts Rich in Compound A (2)

(1) As a pretreatment step for removing water-soluble proteins, chicken meat (200 g) and water (200 g) were introduced into a column in a system and treated at a high temperature under a high pressure with a 400 cc high-temperature high-pressure reactor (AKIKO).

(2) Then, as a heating step, the liquid in the above vessel was isolated and discarded. Water was added in an amount equal to the mass of the chicken meat, and the same treatment as shown in (1) was repeated again at a high temperature under a high pressure.

(3) The resulting liquid was filtered through a strainer of about 40 mesh. Then, the filtrate was centrifuged (6500 rpm, 5 minutes) and further filtered through a strainer (300 mesh), followed by filtration through a 5 μm filter (Sumitomo 3M Limited, Japan).

It should be noted that extract 1 in Table 1 below was not subjected to the pretreatment step.

The pH, the content of compound A and the Bx value were measured for each extract to calculate the ratio of compound A content/Bx.

For determination of Bx values, a Bx meter (RX-5000α: Atago Co., Ltd., Japan) was used for measurement.

The results in Table 1 indicate that when the pretreatment step (1) is performed to remove water-soluble proteins or when pretreatment conditions are set to a higher temperature and a longer time, the extracts obtained in the heating step (2) have lower Bx values. As a result, it is indicated that extracts with a high ratio between the content of compound A (unit: μg/100 g) and Brix (Bx) are obtained.

(1) As a pretreatment step for removing water-soluble proteins, chicken meat (1 kg) and water (1 kg) were introduced into a 2 L pressure-resistant vessel and treated at a high temperature in an autoclave (Tomy Seiko Co., Ltd., Japan, LSX500).

(2) Then, as a heating step, the liquid in the above vessel was isolated and discarded. Water was added in an amount equal to the mass of the chicken meat, and the same treatment as shown in (1) was repeated again at a high temperature.

(3) The resulting liquid was filtered through a strainer of about 40 mesh. Then, the filtrate was centrifuged (6500 rpm, 5 minutes) and further filtered through a strainer (300 mesh), followed by filtration through a 5 μm filter (Sumitomo 3M Limited, Japan).

The thus prepared extracts were subjected to a sensory test. Furthermore, the samples of Nos. 1-10 were each concentrated with an evaporator to give the same compound A content (77.79 μg/100 g) as in No. 11. After concentration, 11 types of extracts containing compound A at the same concentration were obtained and also subjected to a sensory test. The results obtained are shown in Table 2. It should be noted that compound A is expressed as PB in Table 2.

TABLE 1

| Extract | 1 | 2 | 3 | 4 | 5 |
|---|---|---|---|---|---|
| Pretreatment step | — | 160° C. 3 hours | 160° C. 6 hours | 160° C. 9 hours | 160° C. 12 hours |
| Heating step | 160° C. 3 hours | 160° C. 3 hours | 160° C. 3 hours | 160° C. 3 hours | 160° C. 3 hours |
| Compound A Content (μg/100 g) | 137.8 | 138.3 | 106.6 | 109.8 | 104.2 |
| Bx | 11.5 | 4.05 | 1.38 | 0.68 | 0.5 |
| Ratio | 12 | 34.2 | 77.2 | 161.4 | 208.4 |
| pH | 6.7 | 6.8 | 6.6 | 6.4 | 6.2 |

Example 5

First, extracts (sample Nos. 1 to 11) were prepared under 11 different conditions according to steps (1) to (3) shown below.

TABLE 2

| | | No. 1 | No. 2 | No. 3 | No. 4 | No. 5 | No. 6 | No. 7 | No. 8 | No. 9 | No. 10 | No. 11 |
|---|---|---|---|---|---|---|---|---|---|---|---|---|
| Production step conditions | Pretreatment step conditions | — | — | — | — | — | — | 100° C. 0.5 hr | 120° C. 3 hr | 125° C. 3 hr | 130° C. 4 hr | 135° C. 4 hr |
| | Heating step conditions | 120° C. 3 hr | 125° C. 3 hr | 130° C. 3 hr | 135° C. 4 hr | 135° C. 7 hr | 135° C. 10 hr | 130° C. 3 hr | 130° C. 3 hr | 125° C. 3 hr | 130° C. 3 hr | 135° C. 4 hr |
| Analysis data | PB | n.d | 7.43 | 7.9 | 41.86 | 58.48 | 73.19 | 13 | 20.5 | 22 | 48.68 | 77.79 |
| | Brix | 5.5 | 5.5 | 6.5 | 6.9 | 8.3 | 8.9 | 4.85 | 4.8 | 2.4 | 2.6 | 5.4 |
| | PB/Brix | 1.36 | 1.36 | 1.21 | 6.07 | 7.01 | 8.24 | 2.68 | 4.27 | 9.17 | 18.72 | 14.41 |
| Sensory test | Overall flavor | — | ◎ | ◎ | ○ | Δ | X | ◎ | ◎ | ◎ | ◎ | ○ |
| | Bitterness | — | 4 | 4 | 3 | 1 | 1 | 4 | 4 | 3 | 3 | 2 |
| | Chicken odor | — | 4 | 4 | 4 | 3 | 2 | 4 | 4 | 3 | 3 | 3 |
| | Slack | — | 3 | 3 | 3 | 2 | 2 | 3 | 3 | 2 | 2 | 2 |
| PB content adjusted to 77.79 (No. 11) | Concentration factor (fold) | — | 10.47 | 9.85 | 1.86 | 1.33 | 1.06 | 5.98 | 3.79 | 3.54 | 1.60 | 1.00 |
| | Bx after concentration | — | 57.6 | 64.0 | 12.8 | 11.0 | 9.5 | 29.0 | 18.2 | 8.5 | 4.2 | 5.4 |
| | Overall flavor | — | X | X | Δ | Δ | X | X | ○ | ○ | ◎ | ○ |
| | Bitterness | — | 3 | 3 | 2 | 1 | 1 | 2 | 2 | 2 | 3 | 2 |

TABLE 2-continued

| | | | | | | | | | | | |
|---|---|---|---|---|---|---|---|---|---|---|---|
| Chicken odor | — | 1 | 1 | 2 | 3 | 2 | 1 | 2 | 2 | 3 | 3 |
| Slack | — | 0 | 0 | 1 | 1 | 2 | 1 | 2 | 2 | 2 | 2 |

Score table

| | | | | | |
|---|---|---|---|---|---|
| Overall flavor | ◎◎ | Not affecting the flavor of beverages upon addition | Chicken odor | 5 | No chicken odor (unpleasant odor) |
| | ◎ | Substantially not affecting the flavor of beverages upon addition | | 4 | Slight chicken odor (unpleasant odor) |
| | ○ | Slightly affecting the flavor of beverages upon addition | | 3 | Chicken odor (unpleasant odor) |
| | Δ | Strongly affecting the flavor of beverages upon addition | | 2 | Strong chicken odor (unpleasant odor) |
| | X | Extremely strongly affecting the flavor of beverages upon addition | | 1 | Extremely strong chicken odor (unpleasant odor) |
| | XX | Not suitable for use in beverages | | 0 | Too strong in chicken odor (unpleasant odor) to ingest |
| Bitterness | 5 | No bitterness | Slack | 5 | No slack after ingestion |
| | 4 | Slight bitterness | | 4 | Slight slack after ingestion |
| | 3 | Bitterness | | 3 | Slack after ingestion |
| | 2 | Strong bitterness | | 2 | Strong slack after ingestion |
| | 1 | Extremely strong bitterness | | 1 | Extremely strong slack after ingestion |
| | 0 | Too bitter to ingest | | 0 | Too strong in slack after ingestion to ingest |

Example 6

Study on pH of Extract-containing Beverages

Extract 3 of Example 4 above (1 g) was added to liquids (100 ag each), which had been adjusted to various pH values with citric acid and 3Na citrate, to test whether sediment occurred.

As a result, the extract was found to cause no sediment even when added to a liquid of pH 5 or more.

TABLE 3

| | Extract 3 (Example 4) |
|---|---|
| pH = 7 | ○ |
| pH = 6 | ○ |
| pH = 5 | ○ |
| pH = 4 | X |
| pH = 3 | X |

Example 7

Measurement of Compound A and Bx Values in Conventional Products

Commercially available chicken extracts, granular chicken stock or consomme cube were each dissolved in a given amount, and the resulting soups were measured for their compound A content and Bx value to calculate the ratio thereof.

It was confirmed that samples whose ratio exceeds 6 could not be obtained from the commercially available chicken extracts and chicken stock. Even when the chicken consomme cube was used to prepare a soup at a concentration twice as high as the given concentration, the ratio remained unchanged because the Bx value also increased. This also applies to the case where commercially available chicken extracts are concentrated. Namely, it was not possible to produce any extract whose ratio between the content of compound A and Brix is 6 (μg/100 g)/Bx or more by using commercially available products.

TABLE 4

| | Compound A (μg/100 g) | Bx | Compound A/Bx |
|---|---|---|---|
| New Moon's Essence of Chicken | 27 | 10 | 2.7 |
| Scotch's Essence of Chicken | 57.5 | 12 | 4.8 |
| Ajinomoto's granular chicken stock (at a given concentration) | 0.78 | 2.5 | 0.31 |
| Ajinomoto's chicken consommé cube (at a given concentration) | 3.3 | 2.4 | 1.4 |
| Ajinomoto's chicken consommé cube (at a concentration twice as high as the given concentration) | 6.6 | 4.8 | 1.4 |

Example 8

Changes in Compound A and Bx Values Upon Re-heating

The conventionally used heating step was repeated again on a commercially available chicken extract to confirm how the content of compound A and Bx value were changed. The conventionally used heating step is intended to mean a heating step in a pressure cooker for household use. It should be noted that the heating temperature in such a pressure cooker is about 120° C.

The content of compound A slightly increased with the passage of the heating time, but there was no dramatic increase. It was confirmed that the ratio between compound A and Bx remained substantially unchanged in conventional products upon re-heating. Namely, it is indicated that it is also not possible to obtain any extract whose ratio between the content of compound A and Brix is 6 (μg/100 g)/Bx or more even when commercially available chicken extracts are heated again.

TABLE 5

| Material: chicken meat and chicken extract (commercially available) Heating time: 1 hour, 3 hours and 6 hours | | | |
|---|---|---|---|
| Heated sample | Chicken extract | | |
| Heating device | Pressure cooker for household use | | |
| Heating temperature | 120° C. | | |
| Heating time | 1 hr | 3 hr | 6 hr |

TABLE 5-continued

| Material: chicken meat and chicken extract (commercially available) Heating time: 1 hour, 3 hours and 6 hours | | | |
|---|---|---|---|
| Compound A content (ug/100 g) | 25.7 | 26.9 | 28.0 |
| Bx | 9.9 | 9.9 | 10.0 |
| Ratio | 2.0 | 2.1 | 2.2 |
| pH | 6.3 | 6.3 | 6.3 |

Example 9

Production of Beverages Containing Compound A (1)

Extract 3 prepared in Example 4 above was added to prepare beverages. The recipe used is as shown below. Each sample was adjusted to the same Bx value of 10. When compared to the commercially available chicken extract, the starting materials prepared according to this recipe were found to have a higher compound A content even at the same Bx value and further to be excellent in flavor and appearance.

TABLE 6

| | Amount used (g/100 g) | Amount used (g/100 g) | Commercially available product (NMEOC) |
|---|---|---|---|
| Sugar | 9.22 g | 8.84 g | — |
| Extract 3 of Example 4 | 56.3 g | 84.4 | — |
| Water | 34.48 g | 6.76 g | — |
| Bx | 10.0 | 10.0 | 10 |
| pH | 6.6 | 6.6 | 6.4 |
| Compound A (ug/100 g) | 60 | 90 | 25 |
| Ratio (compound A/Bx) | 6 | 12 | 2.5 |
| Flavor | Ingestible without feeling bitterness | Ingestible without feeling bitterness | Slightly bitter aftertaste |
| Appearance | Transparent brown | Transparent brown | Dark brown |

*NMEOC: New Moon's Essence of Chicken

Example 10

Production of Compound A-containing Extract Powder and Beverages

The extract prepared in Example 4 above was lyophilized by spray drying to prepare an extract powder.
1. The extract (extract 3 of Example 4; 100 g) was taken into a 200 ml recovery flask.
2. This flask was stored in a freezer (−18° C.) for 2 or 3 days until the extract was completely frozen.
3. The flask was mounted on a lyophilizer (LABCONCO, set at −40° C. or less) and lyophilized to complete dryness.
4. A dried powder was obtained in a yield of 1.38 g.
5. The powder obtained in 4 above was taken in an amount of 0.817 g and stirred in 99.183 g of water to give an ingestible liquid containing compound A at a concentration of 60 µg/100 g.

INDUSTRIAL APPLICABILITY

The present invention provides extracts and beverages having an improving effect on learning motivation and being highly safe without side effects. The extracts of the present invention can be added to beverages and so on without impairing the taste inherent to foods and beverages. The extracts or beverages of the present invention, as well as foods and beverages comprising the same can be ingested continuously over a long period of time as foods and beverages useful for improvement of learning motivation.

The invention claimed is:

1. A chicken meat extract containing 2,5-piperazinedione, 3,6-bis(phenylmethyl)-,(3S,6S)- and having a pH of 5 or more, wherein the ratio between the soluble content of 2,5-piperazinedione,3,6-bis(phenylmethyl)-,(3S,6S)- (µg/100 g) and Brix (Bx) is 12 to 208.4 (µg/100 g)/Bx.

2. The extract according to claim 1, which contains 2,5 piperazinedione,3,6- bis(phenylmethyl)-,(3S,6S)- at a concentration of 60 µg/100 g or more.

3. A capsule or tablet encapsulating the extract according to claim 1.

4. A beverage containing a chicken meat extract, containing 2,5-piperazinedione,3,6-bis(phenylmethyl)-,(3S,6S)- and having a pH of 5 to 10, wherein the ratio between the soluble content of 2,5-piperazinedione,3,6-bis(phenylmethyl)-,(3S,6S)-(µg/100 g) and Brix (Bx) is 12 to 208.4 (µg/100 g)/Bx.

5. The beverage according to claim 4, which contains 2,5-piperazinedione,3,6-bis(phenylmethyl)-,(3S,6S)- in an amount of 60 µg/100 g or more.

6. A packaged beverage, wherein the beverage according to claim 4 is packed in a container.

7. A process for producing the extract according to claim 1, which comprises:
(1) a pretreatment in which meat of chicken is used as a starting material and heated in a liquid to remove water-soluble proteins contained therein,
(2) a heating in which the liquid is replaced after the pretreatment and heating is repeated again, and
(3) a filtration in which the obtained liquid sample is filtered, thereby obtaining the chicken meat extract of claim 1.

8. A process for producing the extract according to claim 1, which comprises:
(1) a pretreatment in which meat of chicken is used as a starting material and heated in a liquid to remove water-soluble proteins contained therein,
(2) a heating in which the liquid is replaced after the pretreatment and heating is repeated again,
(3) a filtration in which the obtained liquid sample is filtered, and
(4) a concentration,
thereby obtaining the chicken meat extract of claim 1.

9. A process for producing the beverage according to claim 5, which comprises:
(1) a pretreatment in which meat of chicken is used as a starting material and heated in a liquid to remove water-soluble proteins contained therein,
(2) a heating in which the liquid is replaced after the pretreatment and heating is repeated again, and
(3) a filtration in which the obtained liquid sample is filtered,
thereby obtaining the beverage containing a chicken meat extract of claim 5.

10. A process for producing the beverage according to claim 4, which comprises:
(1) a pretreatment in which meat of chicken is used as a starting material and heated in a liquid to remove water-soluble proteins contained therein, (2) a heating in which the liquid is replaced after the pretreatment and heating is repeated again, and
(3) a filtration in which the obtained liquid sample is filtered, and
(4) a concentration, thereby obtaining the beverage containing a chicken meat extract of claim 4.

* * * * *

UNITED STATES PATENT AND TRADEMARK OFFICE
CERTIFICATE OF CORRECTION

| | | |
|---|---|---|
| PATENT NO. | : 10,532,079 B2 | Page 1 of 1 |
| APPLICATION NO. | : 15/082526 | |
| DATED | : January 14, 2020 | |
| INVENTOR(S) | : Hideki Matsubayashi et al. | |

It is certified that error appears in the above-identified patent and that said Letters Patent is hereby corrected as shown below:

On the Title Page

(71) Applicants, please change:
"SUNTORY HOLDINGS LIMITED, Osaka (JP); CEREBOS PACIFIC LIMITED, China Square Central (SG)"

To:
-- SUNTORY HOLDINGS LIMITED, Osaka (JP); SUNTORY BEVERAGE & FOOD ASIA PTE. LTD., Singapore (SG) --

Signed and Sealed this
Twelfth Day of May, 2020

Andrei Iancu
*Director of the United States Patent and Trademark Office*